United States Patent
Witte et al.

(10) Patent No.: US 10,675,407 B2
(45) Date of Patent: Jun. 9, 2020

(54) TUNGSTEN CONTAINING FORMING MANDREL FOR GLASS FORMING

(71) Applicant: SCHOTT AG, Mainz (DE)

(72) Inventors: Joerg Witte, Pfungstadt (DE); Xaver Jud, Neukirch a. d. Thur (CH); Alexander Humbertjean, Engelburg (CH)

(73) Assignee: SCHOTT AG, Mainz (DE)

( * ) Notice: Subject to any disclaimer, the term of this patent is extended or adjusted under 35 U.S.C. 154(b) by 322 days.

(21) Appl. No.: 15/292,954

(22) Filed: Oct. 13, 2016

(65) Prior Publication Data

US 2017/0119967 A1 May 4, 2017

(30) Foreign Application Priority Data

Oct. 13, 2015 (DE) .......................... 10 2015 117 422

(51) Int. Cl.
| | |
|---|---|
| *A61M 5/178* | (2006.01) |
| *C03B 23/045* | (2006.01) |
| *C03B 23/055* | (2006.01) |
| *C22C 5/04* | (2006.01) |
| *C03B 23/09* | (2006.01) |
| *C03B 23/043* | (2006.01) |
| *C03B 23/049* | (2006.01) |

(52) U.S. Cl.
CPC ........... *A61M 5/178* (2013.01); *C03B 23/043* (2013.01); *C03B 23/045* (2013.01); *C03B 23/049* (2013.01); *C03B 23/055* (2013.01); *C03B 23/092* (2013.01); *C22C 5/04* (2013.01); *A61M 2207/00* (2013.01); *A61M 2207/10* (2013.01)

(58) Field of Classification Search
CPC ... C03B 23/043; C03B 23/045; C03B 23/049; C03B 23/092; C03B 23/055; C22C 5/04; A61M 2207/00; A61M 2207/10; A61M 5/178
See application file for complete search history.

(56) References Cited

U.S. PATENT DOCUMENTS

| | | | |
|---|---|---|---|
| 2,376,742 | A | 5/1945 | Wempe |
| 2,933,590 | A | 4/1960 | Leedy et al. |
| 3,371,409 | A | 3/1968 | Bonnet |
| 2003/0046956 | A1 | 3/2003 | Anderson |
| 2008/0282734 | A1 | 11/2008 | Kolberg et al. |
| 2011/0016925 | A1 | 1/2011 | Morrill, Jr. |

(Continued)

FOREIGN PATENT DOCUMENTS

| | | |
|---|---|---|
| CH | 375494 | 2/1964 |
| DE | 102007023497 | 11/2008 |

(Continued)

*Primary Examiner* — Seyed Masoud Malekzadeh
(74) *Attorney, Agent, or Firm* — Ohlandt, Greeley, Ruggiero & Perle, L.L.P.

(57) ABSTRACT

A molding tool, a method, and an apparatus for hot forming of glass are provided that provide glass products used for pharmaceutical packaging. The molding tool includes a forming mandrel for reshaping at least a portion of a heated region of a glass precursor. The mandrel has a temperature-stable core material and an alloying element. The core material is made of precious metals, in particular of platinum group elements, and the further alloying element is made of one of tungsten, zirconium, rhodium, molybdenum, and rhenium.

23 Claims, 5 Drawing Sheets

(56) References Cited

U.S. PATENT DOCUMENTS

2015/0114043 A1* 4/2015 Risch ................... C03B 23/043
65/29.18
2016/0002087 A1* 1/2016 Prais ................... A61M 5/3134
65/108

FOREIGN PATENT DOCUMENTS

| DE | 102012101948 | 9/2013 | |
|----|--------------|--------|---|
| DE | 102012101948 A1 * | 9/2013 | ........... C03B 23/043 |
| EP | 1471040 | 10/2004 | |
| EP | 1809579 | 8/2012 | |
| WO | 2006039705 | 4/2006 | |
| WO | 2006073841 | 7/2006 | |
| WO | 2012085619 | 6/2012 | |

* cited by examiner

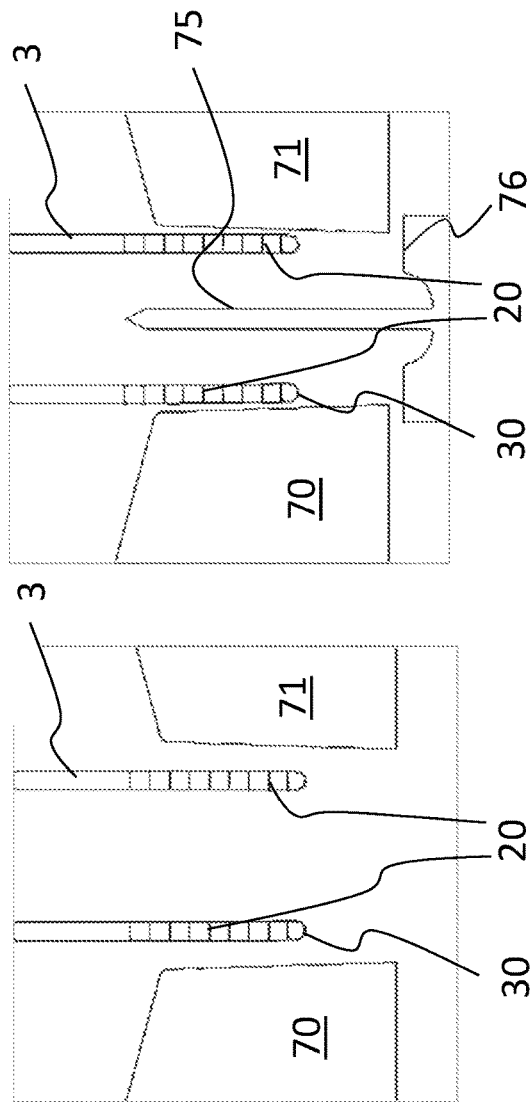
Fig. 3A
Fig. 3B
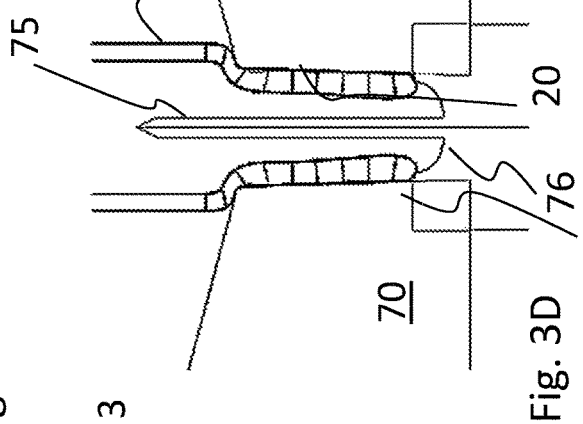
Fig. 3C
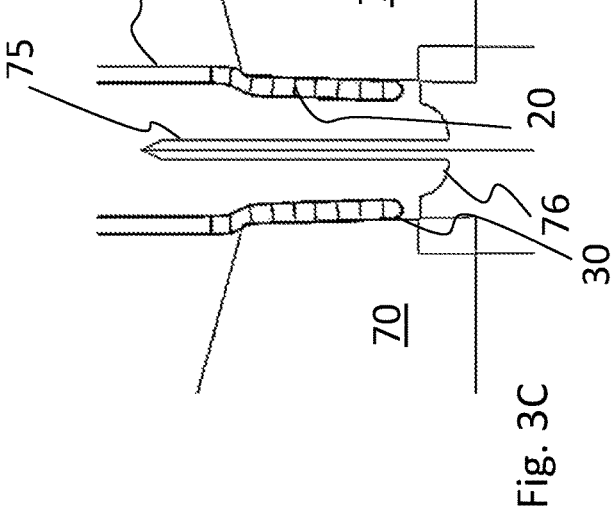
Fig. 3D

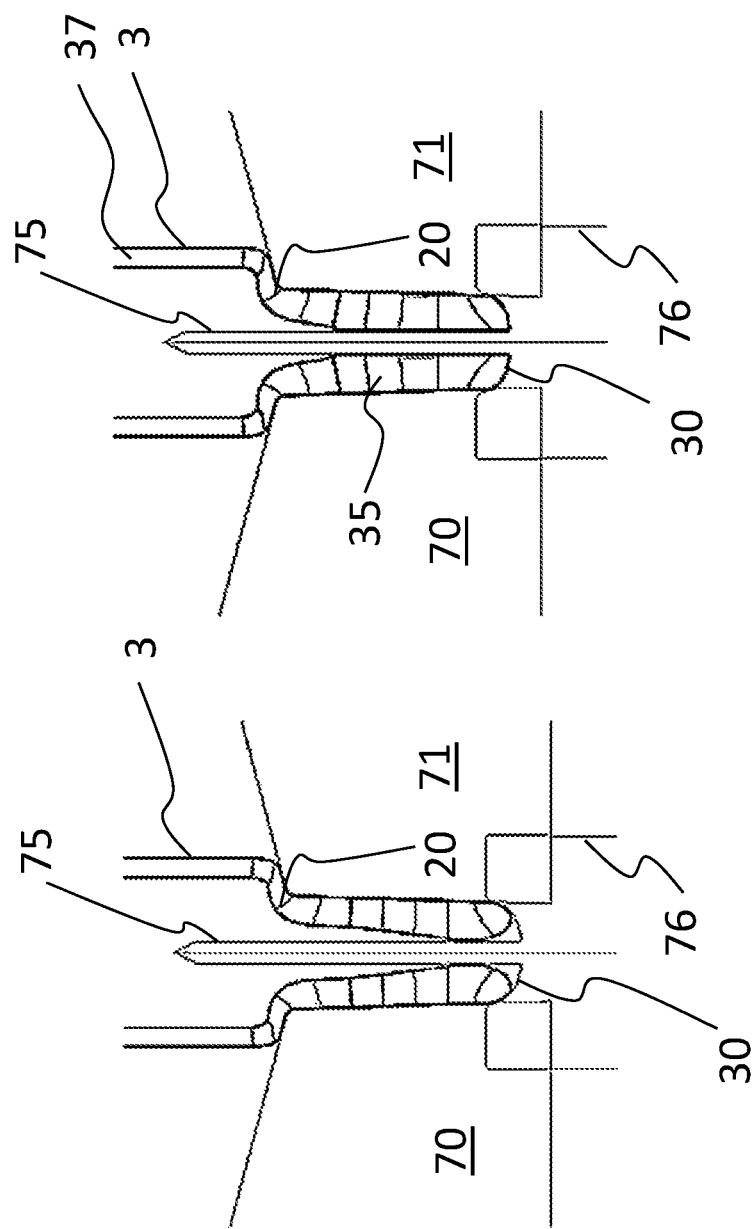

TUNGSTEN CONTAINING FORMING MANDREL FOR GLASS FORMING

CROSS REFERENCE TO RELATED APPLICATIONS

This application claims the benefit under 35 U.S.C. 119 of German Application No. 10 2015 117 422.7 filed on Oct. 13, 2015, the contents of which are incorporated herein in their entirety.

BACKGROUND

1. Field of the Invention

The invention generally relates to the manufacturing of glass products. More particularly the invention relates to a molding tool which comprises a tungsten-containing forming mandrel, to a method and to an apparatus for hot forming of glass. The glass products obtained in this way can be used as a pharmaceutical packaging, for example.

2. Description of Related Art

In the manufacturing of hollow-body glass products, hot forming is an essential process step. The process flow in hot forming usually comprises a plurality of successive heating and molding processes performed to produce the desired final geometry starting from tubular glass bodies.

Hollow-body glass products that are to be used in the medical field are usually subject to very high requirements in terms of possible contamination resulting from the hot forming process. This implies stringent requirements on the molding tools used in hot forming. These stringent requirements in particular concern the materials used for the molding tools. For example, when making hollow-body glass products typically a cone is formed using a molding tool that comprises a forming mandrel. The material of the forming mandrel plays a crucial role in this case.

In the production of pharmaceutical packaging or in the hot forming of medical storage containers made of glass for pharmaceuticals, such as ampoules, syringes, vials, cartridges, metallic forming materials may be employed as a forming mandrel material.

Pure tungsten or tungsten alloys exhibit high thermomechanical resistance which is highly beneficial in particular in the case of small material cross sections. This is the case, for example, with forming mandrels which have a diameter of less than 0.5 mm to about 1 mm. Therefore, mandrels which comprise tungsten or tungsten alloys in the contact area to the glass to be reshaped are advantageous.

For example, when producing syringes from tubular glass bodies which is usually accomplished on indexed machines, e.g. rotary transfer machines, the forming mandrel is heated to temperatures of about 800° C. to 900° C. during hot forming. Because of the short cycle times, the material is subjected to frequent and rapid temperature changes. The influence of temperature, glass evaporation products, air, moisture, and the tribological load due to the doughy glass that is pressed against the mandrel during hot forming may therefore cause material erosion on the forming mandrel.

This material erosion on the forming mandrel, in particular in the contact area to the glass precursor to be reshaped, is generally undesirable and causes an alteration in the outer geometry or a reduction in diameter of the forming mandrel, and moreover this reduction in diameter is often not uniform in axial direction. This material erosion has several other negative effects.

For example, as a result of material erosion the predetermined nominal dimensions for shaping will be less and less respected over time, due to the altered outer geometry of the forming mandrel, and so the required channel dimensions can only be met for a limited time period. Thus, the service life of the forming mandrel is comparatively low and/or additional effort will be required for subsequent adjustments. Furthermore, the eroded material might get into the interior of the glass product just formed. During shaping of syringe cones, for example, eroded material might be introduced into the so-called cone channel.

Pharmacologically active substances that are stored in the syringes, however, might interact with the tungsten-containing contaminations in the interior of the glass product, so that the effectiveness thereof might be altered. Therefore, for special pharmaceuticals there exists an increasing demand for glass vessels which meet a specified upper limit of tungsten content or which are even entirely free of tungsten.

Given this background, mandrels have been developed which are free of tungsten. For preventing tungsten-containing contaminations, document EP 1 809 579 B1, for example, proposes to use a forming mandrel which does not contain any tungsten.

Document EP 1 471 040 A1 discloses a forming mandrel which is free of tungsten and comprises graphite as an essential material. Moreover the forming mandrel may include other materials such as silicon carbide or zirconium carbide, and therefore it is free of tungsten.

Furthermore, document WO 2006/039705 A2 proposes a forming mandrel which comprises a protective layer in the form of an overlay layer. The base material may contain tungsten in this case. For the layer material, a material contained in neutral glass is proposed, or a glass which constitutes a component of the glass to be reshaped, in order to prevent foreign contaminants in this way.

Generally, such coatings are subject to a certain amount of wear so that the adverse effect of material erosion of the forming mandrel can hardly be prevented. Therefore, the service life of such a forming mandrel is rather low. Furthermore, cracking of layer material or chipping of layer components may occur due to the high mechanical stress, so that the service life of the forming mandrel is further reduced.

On the other hand, a low tungsten content in the interior of the formed part does not represent great disadvantages for a multitude of formed glass products, provided that the tungsten content remains in a predetermined range or does not exceed a tolerable limit.

SUMMARY

The object of the present invention resulting therefrom is to provide a material for a molding tool, in particular for a forming mandrel, as well as a method and an apparatus for forming hollow-body glass products.

Introduction of unwanted impurities, in particular of tungsten, into the glass product to be reshaped by the molding tool, in particular by the forming mandrel, shall remain within a predetermined range. In particular the interior or the inner cone of the reshaped glass product shall not exceed a predetermined limit in contamination from the molding tool, in particular the forming mandrel.

Furthermore, the molding tool, in particular the forming mandrel, shall have a long service life. Material erosion shall possibly be prevented, so that a particularly long service life can be achieved with consistent quality and without additional adjustment effort.

Moreover, spalling of outer components of the molding tool, in particular the forming mandrel, should substantially be eliminated.

Finally, the risk of cracking in the surface of the forming mandrel should be avoided.

Accordingly, the invention relates to a molding tool for reshaping hollow-body glass precursors, the molding tool comprising a forming mandrel for reshaping at least a portion of a heated region of the glass precursor.

The forming mandrel is made of an alloy which comprises at least a first temperature-stable 76 material. Preferably, the forming mandrel is a solid forming mandrel to achieve greatest possible stability. In conjunction with this document, the term core material refers to the basic or base material of the forming mandrel from which it is made.

A material particularly suitable as a core material for the forming mandrel is a material that exhibits high heat resistance and a high modulus of elasticity so as to be appropriate for the mechanical stresses even at temperatures in the range of 400° C. or more. Furthermore, it should be resistant to acids and glass evaporation products such as borates and should exhibit resistance to oxidation in air up to 400° C. in order to avoid material erosion during or by the hot forming processes for reshaping hollow-body glass precursors.

Therefore, the core material is selected from the group of precious metals, in particular of platinum group elements. The core material may as well comprise an alloy. Suitable core materials include the precious metals and their alloys, such as platinum.

In addition to the core material the forming mandrel comprises a further alloying element which is selected from the group consisting of tungsten, zirconium, rhodium, molybdenum, ruthenium, and rhenium.

The inventors have found that besides the prior art forming mandrels made of tungsten, forming mandrels including alloys of platinum group elements are very well suited as a molding tool as well, in particular as a core material for a forming mandrel, since they exhibit high mechanical strength.

It was demonstrated that even small additions of the further alloying element tungsten, zirconium, rhodium, molybdenum or rhenium allow to significantly improve the mechanical and structural behavior of the forming mandrel. The mechanical and structural enhancement of the forming mandrel is particularly advantageous if the material iridium is selected as the core material.

What was completely unexpected with such a molding tool which included iridium as a core material and tungsten as a further alloying element was that the introduction of tungsten into the glass product to be reshaped is very low. This is particularly surprising since it is generally known that the use of tungsten-containing materials as a molding tool, in particular as a forming mandrel, leads to a rather strong tungsten contamination of the reshaped product, in particular in the interior of the reshaped product. Given this background, document EP 1 809 579 B1 recommends the use of tungsten-free forming mandrels, for example.

Therefore, surprisingly, the interior and in particular the inner cone of the reshaped glass product can be kept virtually free of impurities, in particular free of contamination with tungsten, although the forming mandrel includes an amount of tungsten.

Besides iridium, the core material of the forming mandrel may also comprise palladium, platinum, rhodium, rhenium, and/or ruthenium, or an alloy comprising iridium, palladium, platinum, rhodium, rhenium and/or ruthenium.

In one embodiment the core material comprises at least 20 wt % of platinum or an alloy including at least 20 wt % of platinum.

In another embodiment the core material comprises at least 5 wt % of rhodium or an alloy including at least 5 wt % of rhodium.

In a further preferred embodiment, the core material comprises a platinum-rhodium alloy including at least 20 wt % of platinum, preferably 25 wt % of platinum, and more preferably 30 wt % of platinum, and at least 5 wt % of rhodium, preferably at least 7 wt % of rhodium, and more preferably at least 10 wt % of rhodium.

In yet another embodiment the core material comprises a platinum-nickel alloy including at least 5 wt % of nickel.

In yet another preferred embodiment the core material comprises a platinum-iridium alloy including at least 5 wt % of iridium, preferably at least 10 wt % of iridium, and more preferably at least 20 wt % of iridium.

In yet another preferred embodiment the core material comprises at least 20 wt % of iridium, preferably at least 50 wt % of iridium, more preferably at least 70 wt % of iridium, and most preferably at least 90 wt % of iridium as an alloying element.

The inventors have found that already very small additions of alloying elements such as tungsten, zirconium, rhodium, molybdenum or rhenium may significantly improve the mechanical and structural behavior of the alloy for the forming mandrel. The amount of these alloying elements is advantageously in a range of at least 0.1 wt %, preferably at least 0.3 wt %, more preferably 0.5 wt % and most preferably at least 0.9 wt %, and not more than 10 wt %, preferably at most 6 wt %, and more preferably at most 5 wt %.

In a particularly preferred embodiment, iridium is chosen as the core material and tungsten as the alloying element.

Iridium or high iridium content alloys exhibit very high hardness, which on the one hand is an immanent property of the material, but can as well be achieved by strain hardening during manufacture thereof. Due to the high recrystallization temperature of iridium, this strength or hardness will largely be preserved even when employed at temperatures of around 800° C. or 900° C. which may occur in hot shaping.

Tungsten is distinguished by a high resistance to acids such as HF and HCl and is only slightly attacked by sulfuric acid. Furthermore, it exhibits good oxidation resistance in air up to 400° C. In addition, a high heat resistance and a high modulus of elasticity are favorable for use as an alloying material for a forming mandrel.

It has been found that already very small amounts of tungsten as an alloying element have a positive influence on the strength of the mandrel. The very small amounts of tungsten are in a weight percentage range starting from about 0.01 wt %.

Therefore, a very advantageous material for the forming mandrel is a material comprising an iridium-tungsten alloy with at least 0.01 wt %, 0.05 wt %, 0.1 wt %, preferably at least 0.3 wt %, more preferably at least 0.5 wt %, and most preferably at least 1 wt % of tungsten. It is furthermore advantageous if the tungsten content is not more than 10 wt %, preferably not more than 6 wt %, and more preferably at most 5 wt %.

The very suitable material for the forming mandrel may comprise, for example, an iridium-tungsten alloy with 0.96 wt %, 1.92% wt %, or 3.84 wt % of tungsten.

Such a material exhibits increased tensile strength and reduced elongation at break. For example, an iridium-tungsten alloy with 0.96 wt % of tungsten exhibits a yield strength of 16.271 kN/cm$^2$. Tensile strength is 39.989 kN/cm$^2$, and elongation at break is 16.823 kN/cm$^2$.

Furthermore, it was observed that the grain size of such an iridium-tungsten alloy was reduced and recrystallization temperature increased. This had a very positive effect on chipping of outer components of the molding tool and on the risk of cracking at the surface of the forming mandrel. In this manner it was possible to significantly improve the service life of a forming mandrel made of an iridium-tungsten alloy as the forming mandrel material.

Compared to precious metals platinum and rhodium, iridium has the highest volatility in an oxygen containing atmosphere at elevated temperature. At temperatures of more than about 900° C., iridium oxides $IrO_2$ and $IrO_3$ will be formed. These oxides are volatile, they sublimate at about more than 1000° C.

Compared to pure iridium, a tungsten content of an iridium-tungsten alloy between 1 wt % and 3 wt % is capable of significantly reducing the mass loss over time. Surprisingly, therefore, such an iridium-tungsten alloy results in a very long service life on the one hand, and on the other in a very low introduction of tungsten into the interior or the cone channel of the glass precursor to be reshaped, due to the very low mass loss over time.

Moreover, resistance to oxidation in air was improved significantly, which has a very positive influence on corrosion wear of the forming mandrel in use.

For the above reasons, iridium alloys with an alloying addition of tungsten are therefore especially suitable for being used as a forming mandrel in hot shaping of the cone channel.

Such iridium-tungsten alloys may be manufactured by a pyrometallurgical process. The forming process of the mandrel may be performed by wire drawing, optionally with a subsequent grinding process to improve surface finish.

Furthermore, the invention provides an apparatus for reshaping hollow-body glass products, comprising: means for locally heating a region of a glass precursor to above its softening point; and at least one molding tool for reshaping at least a portion of the region of a glass precursor that is heated by the means for locally heating, wherein the molding tool comprises a forming mandrel according to the invention.

The forming mandrel is made of an alloy comprising at least a first temperature-stable core material and at least one further alloying element, wherein the core material comprises at least 50 wt % and is selected from the group of precious metals, in particular of platinum group elements, and wherein the further alloying element is selected from the group comprising tungsten, zirconium, rhodium, molybdenum, and/or ruthenium, or rhenium.

During the reshaping process, a portion of the surface of the forming mandrel may be in direct contact with the glass precursor.

The apparatus may comprise a burner for local heating, and additionally rotation means are provided to rotate the forming tool and the glass precursor relative to each other.

The molding tool may furthermore comprise a pair of rollers arranged so that the rollers of the roller pair are rolling on the surface of a glass precursor that is rotated by the rotation means while the laser light is illuminating an area of the circumferential surface of the glass precursor lying between the rollers.

In a further embodiment, the apparatus may further comprise a laser for local heating. In this case, the molding tool is preferably designed so that a surface area of the portion to be reshaped of the glass precursor is not covered by the molding tool, and the laser or an optical system downstream of the laser is arranged so that during reshaping the laser light is irradiated onto the area not covered by the molding tool, and a control device is provided which controls the laser so that the glass precursor is at least temporarily heated by the laser light during the reshaping process.

For heating the glass of a glass precursor to be reshaped in the apparatus, a laser is used which emits light of a wavelength to which the glass of the glass precursor is at the most partially transparent, so that the light is at least partially absorbed in the glass.

The method for reshaping glass products which can be performed with such an apparatus is accordingly based on the steps of: locally heating a hollow-body glass precursor to above its softening point; and reshaping, with at least one molding tool, at least a portion of a region of the glass precursor that has been heated by means for locally heating, wherein the molding tool comprises a forming mandrel according to the invention as described above; and wherein the glass precursor and the molding tool are rotated relative to each other by rotation means.

The molding tool of the invention is particularly suitable for producing pharmaceutical glass packaging with low contamination.

Accordingly, the invention also relates to a glass syringe produced or producible by a method as described above, and which has only very little contamination, in particular only very little tungsten contamination in particular in the interior thereof or in the region of the reshaped inner cone.

A glass syringe produced by the aforementioned method or by means of the aforementioned molding tool can therefore have a low content of tungsten in its cavity.

The tungsten content can be determined by neutron activation analysis (NAA) which is a nuclear physics method for quantitative analysis of the elemental or isotopic composition of samples which are irradiated with neutrons for this purpose. As a result, the atomic nuclei to be detected of the sample, also referred to as analyte nuclei, will interact with the neutrons, and depending on the type of nuclear reaction different products may be created. This process can be performed in a research reactor or by using a different neutron source. The resulting activation products might be radioactive and will then decay with their characteristic half-life. Both during activation and during decay radiation will be released with characteristic energies which can be exploited for the analysis.

Syringes produced according to the invention have a very low tungsten content. With a detection limit of 3 ng which can be achieved with conventional chemical analysis methods no tungsten components are detected. In neutron activation analysis the detection limit is significantly lower, at about 0.03 ng and even down to 0.006 ng. In one case, a tungsten content of about 0.006 ng per syringe was detected.

Therefore, the content of tungsten of the syringe is >0, which is due to wear, albeit very low, of the forming mandrel, and which was determined after a cycle of 100,000 reshaping operations. Based on the wear, a contamination of a syringe by a reshaping operation according to the invention was calculated to be in a range from 0.01 to 0.03 ng per syringe.

Therefore, the tungsten content of a syringe is >0 ng, >0.006 ng, >0.01 ng, >0.03 ng.

The content of tungsten within the cavity is at most 100 ng, at most 50 ng, at most 10 ng, preferably at most 1 ng, and most preferably at most 0.1 ng per syringe.

Such a low contamination is not harmful for the majority of glass products, so that the forming mandrel according to the invention may contribute to significant cost saving potentials, because of its very long service live.

The detection of tungsten contamination is accomplished using an aqueous extraction method in which the internal volume of the syringe is washed with purified water. In this case, the filling volume corresponds to the intended filling volume of the syringe. This is done at elevated temperature (typically 50° C. up to 100° C. and more) and over a period of 4 days. Chemical detection of tungsten is made in the eluate, by inductively coupled plasma mass spectrometry (ICP-MS).

Another advantage of the invention is that coating of the forming mandrel in the contact area can be dispensed with, and thus there will not be any interleaving between the core material and the coating due to a difference in the expansion behavior thereof, whereby the risk of chipping of outer components of the forming mandrel is largely reduced. At the same time the risk of cracking is minimized.

The long service life of the forming mandrel enables manufacturing with consistently high quality of the reshaped glass product without any need for frequent additional adjustment operations on the reshaping apparatus. Thus, a particularly high degree of dimensional accuracy is ensured, since material erosion on the forming mandrel is reduced. This permits to meet tight tolerances with respect to the geometry of the glass product.

Another big advantage is that due to the lower corrosion wear significantly less particles are deposited in the contact area to the glass precursor to be reshaped, for example in the contact area to the cone channel of a syringe. At the same time, significantly less volatile tungsten components are introduced into the interior of the hollow-body glass product such as the interior of the syringe. Thus, the tungsten content detectable by chemical analysis is considerably reduced. Therefore, the molding tool according to the invention, in particular the forming mandrel according to the invention is particularly suitable for use in hot forming of glass products which are used as pharmaceutical packaging.

BRIEF DESCRIPTION OF THE DRAWINGS

The invention will now be described in more detail by way of preferred embodiments and with reference to the accompanying figures. Further details of the invention will be apparent from the description of the illustrated exemplary embodiments and the appended claims.

FIGS. 3A-3F are sectional views through a tubular glass during the reshaping process;

DETAILED DESCRIPTION

Figure 1:
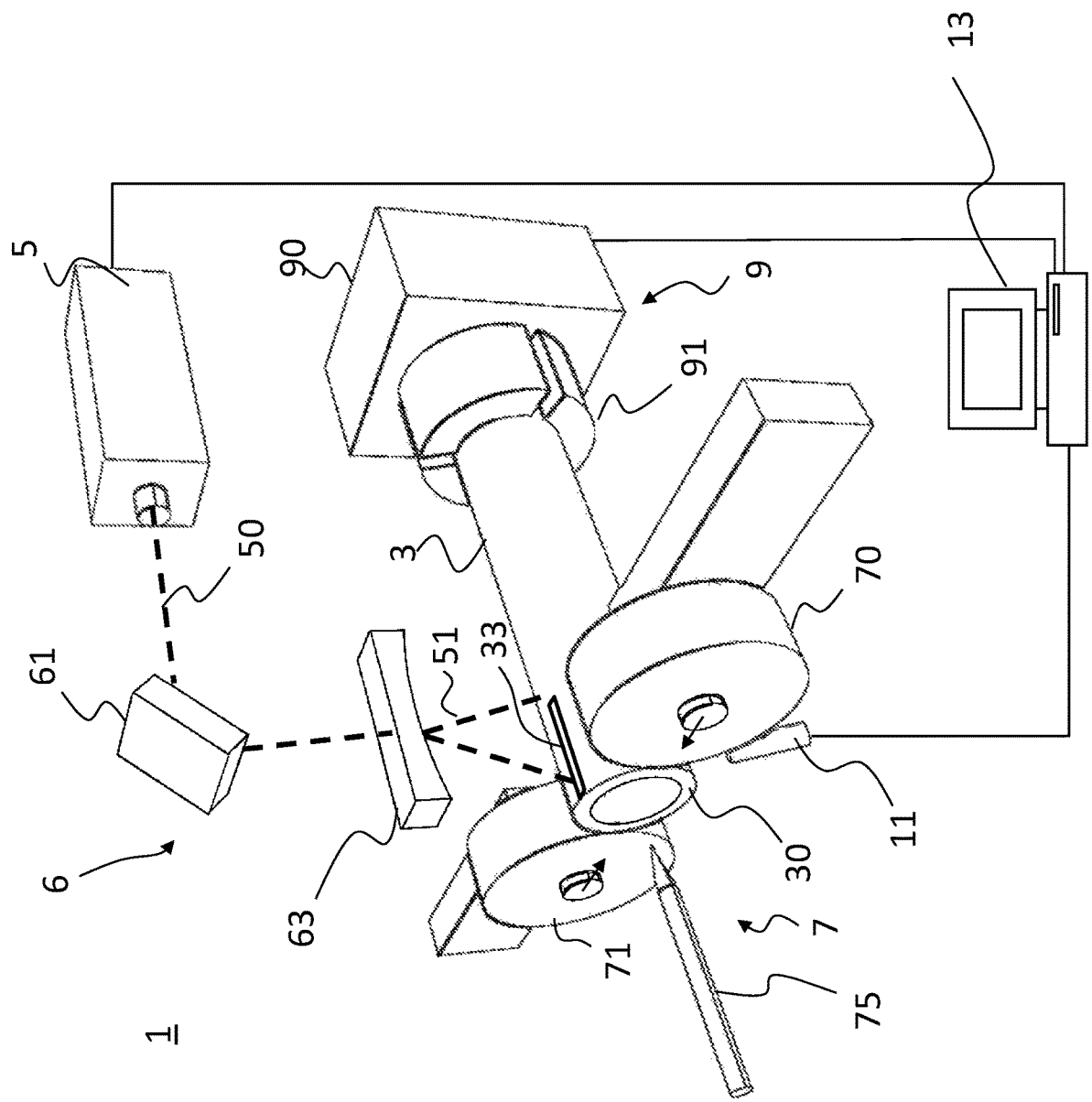
FIG. 1 illustrates components of an apparatus for reshaping tubular glass.

In the following detailed description of preferred embodiments, similar components in or on these embodiments are designated by the same reference numerals, for the sake of clarity. However, in order to better illustrate the invention, the preferred embodiments shown in the figures are not always drawn to scale.

FIG. 1 illustrates an exemplary embodiment of an apparatus 1 for performing the method of the invention.

The apparatus designated by reference numeral 1 as a whole of the exemplary embodiment shown in FIG. 1 is configured for reshaping glass precursors in the form of tubular glass 3. Specifically, the apparatus is used for producing glass syringe bodies, and the elements of apparatus 1 shown in FIG. 1 serve to form the cone of the syringe body from the tubular glass.

The generation of the cone from the tubular glass by means of apparatus 1 basically comprises local heating of a region of a tubular glass 3 to above the softening point thereof, here the end 30 thereof, and reshaping of at least a portion of the heated end using at least one molding tool. In the illustrated example, the means for locally heating comprise a laser 5 which emits light of a wavelength to which the glass material of glass tube 3 is at most partially, i.e. not fully transparent, so that the light is at least partially absorbed in the glass.

Instead of the laser 5 for locally heating a hollow-body glass precursor as illustrated in FIG. 1, it is of course also possible to use other means for local heating which are typically employed for glass hot forming processes. This may be a burner, for example, such as a gas burner. Since the use of such devices is well known, a detailed description thereof is omitted here.

The laser beam 50 of FIG. 1 is directed onto the tubular glass 3 by means of an optical system 6. During the reshaping process, the molding tool 7 and the glass precursor 3 are rotated relative to each other, by rotation means 9. As in the illustrated example, it will usually be favorable to rotate the tubular glass 3 with the axis of rotation along the axial extension of the tubular glass 3. For this purpose, rotation means 9 comprise a drive 90 with chuck 91 which holds the tubular glass 3. Another possibility would be an inverted configuration in which the tubular glass is fixed and the molding tool 7 rotates around the tubular glass.

In the exemplary embodiment shown in FIG. 1, molding tool 7 comprises two rollers 70, 71 which roll on the surface of the tubular glass 3 while the latter is rotated. The end 30 of tubular glass 30 is compressed by driving the rollers to approach each other in the radial direction of tubular glass 3. The radial movement is illustrated in FIG. 1 by arrows on the axes of rotation of rollers 70, 71.

Furthermore, a forming mandrel 75 is provided as a component of molding tool 7. This forming mandrel 75 is introduced into the opening of tubular glass 3 at the end 30 to be reshaped. Using forming mandrel 75, the cone channel of the syringe body is formed. Forming mandrel 75 may be rotatably mounted so as to rotate together with tubular glass 3. It is also possible to have the rotating glass sliding on and around the stationary forming mandrel.

To avoid adhesion, a releasing agent or lubricant which reduces friction in the sliding movement can be used for this purpose, as is usual with molding tools sliding over a glass surface. Furthermore, it is possible to use a lubricant which evaporates at the temperatures employed during reshaping. If such a lubricant is used, lubricant or releasing agent residues on the finished glass product can advantageously be avoided.

Between rollers 70, 71 the laser beam 50 can be directed onto the tubular glass without having the laser beam 50 interrupted by the molding tool. Accordingly, the molding tool is configured so that a surface region of the portion to be reshaped of the tubular glass is not covered by the molding tool, so that by means of optical system 6 arranged downstream of the laser the laser light is irradiated onto the region not covered by the molding tool during the reshaping process. Specifically, an area 33 between rollers 70, 71 on the circumferential surface of the tubular glass 3 is illuminated by the laser light.

The reshaping process is controlled by a control device 13. In particular, control device 13 drives the laser 5 so that during the reshaping process the tubular glass 3 is at least temporarily heated by the laser light.

Optical system 6 of the apparatus shown in FIG. 1 comprises a deflection mirror 61 and a cylindrical lens 63.

Cylindrical lens 63 is provided for expanding the laser beam 50 into a fan beam 51 along the axial direction of the tubular glass 3 so that the area 33 illuminated by the laser light is expanded accordingly in the axial direction of tubular glass 3. Since tubular glass 3 is rotated while the laser light is irradiated, the irradiated power is distributed circumferentially on the tubular glass, so that a cylindrical portion is heated, or more generally, regardless of the shape of the glass precursor, a region in the axial direction along the rotation axis. This region has a length which is preferably at least as long as the portion to be reshaped. The latter has a length which is substantially determined by the width of the rollers. To achieve special laser power distributions in the axial direction of the tubular glass, it is also possible, alternatively or in addition to the cylindrical lens 63, to advantageously use a diffractive optical element.

The forming process is controlled by control device 13. Among other things, control device 13 controls the laser power. Furthermore, the movement of molding tools 70, 71, 75 is controlled. Also, rotation means 9 can be controlled, in particular the rotational speed of drive 90, optionally also the opening and closing of chuck 91.

When forming glass syringe bodies, a radiation power of less than 1 kilowatt will generally be sufficient for the laser 5 to ensure rapid heating to the softening temperature. Once the intended temperature for hot forming has been reached, the laser power may then be reduced by control device 13 so that the incident laser power only compensates for cooling. When producing syringe bodies, between 30 and 100 watts will generally be sufficient for this purpose.

Controlling of the laser power may in particular be accomplished based on the temperature of the tubular glass 3. For this purpose, a control process may be implemented in control device 13, which controls the laser power based on the temperature as measured by a temperature measuring device so as to adjust a predetermined temperature or a predetermined temperature/time profile on the glass precursor. In the example shown in FIG. 1, a pyrometer 11 is provided as the temperature measuring device, which measures the thermal radiation of the tubular glass at the end 30 heated by laser 5. The measured values are supplied to control device 13 and used in the control process for adjusting the desired temperature.

A particular advantage of the setup as exemplified in FIG. 1 is that the laser light is not directly heating the molding tools. As a result thereof, although the glass precursor is heated during the reshaping process, the molding tools will usually not be heated more than in a process with preceding heating using a burner. Overall, less thermal energy is produced in this way, and moreover this thermal energy is introduced into the glass precursor more selectively. Thus, heating of the entire apparatus is reduced, and therefore also running-in phenomena caused by thermal expansions, inter alia.

A preferred glass for the production of syringe bodies is borosilicate glass. Particularly preferred is low-alkali borosilicate glass, in particular with an alkali content of less than 10 percent by weight. Borosilicate glass is generally well suited due to its typically high thermal shock resistance which is favorable to realize rapid heating ramps at the fast processing times that can be achieved with the invention.

A suitable low-alkali borosilicate glass comprises the following constituents, in percent by weight:

| | |
|---|---|
| $SiO_2$ | 75 wt % |
| $B_2O_3$ | 10.5 wt % |
| $Al_2O_3$ | 5 wt % |
| $Na_2O$ | 7 wt % |
| CaO | 1.5 wt % |

Figure 2:
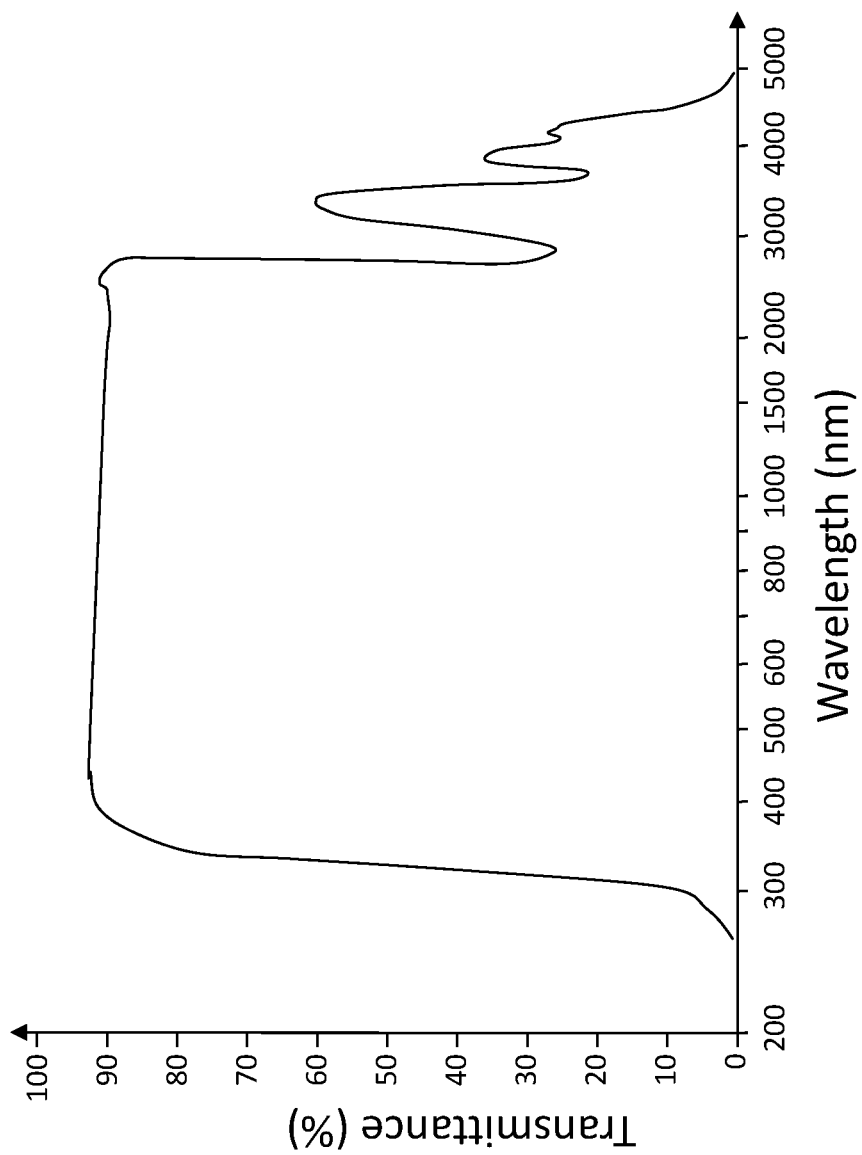
FIG. 2 shows a transmission spectrum of a glass of a glass precursor.

FIG. 2 shows a transmission spectrum of the glass. The transmittance values given refer to a glass thickness of one millimeter. As can be seen from FIG. 2, transmittance of the glass decreases at wavelengths above 2.5 micrometers. Above 5 micrometers the glass is substantially opaque, even in case of very thin glass thicknesses.

The decrease in transmittance in the wavelength range above 2.5 micrometers as shown in FIG. 2 does not significantly depend on the exact composition of the glass. Thus, in preferred borosilicate glasses the contents of the constituents given above may even deviate by 25% from the respective given value, with similar transmission properties. Furthermore, glasses other than borosilicate glass may of course be used as well. As long as these glasses are at most partially transparent, i.e. not fully transparent at the wavelength of the laser, a laser source can be used for heating.

FIGS. 3A to 3F are sectional views schematically illustrating a simulation of a reshaping process according to the invention for forming a syringe cone from a tubular glass 3 in order to produce a syringe body. The sections of the drawings are taken along the center axis of the tubular glass 3 around which the tubular glass is rotated. Rollers 70, 71 and forming mandrel 75 can also be seen.

Lines 20 as indicated in the sectional views of the tubular glass and initially extending perpendicularly to the center axis of the tubular glass are imaginary boundary lines of axial sections of the tubular glass 3. These lines are intended to illustrate the material flow during reshaping.

Forming mandrel 75 protrudes from a foot 76 which serves to shape the distal cone surface of the syringe. Foot 76 is a flat component perpendicular to the viewing direction of FIGS. 3A to 3F. Other than illustrated, the foot is rotated by 90° about the longitudinal axis of forming mandrel 75 in the actual apparatus, so that foot 76 fits between rollers 70, 71. That is to say, the overlapping of rollers 70, 71 and foot 76 as seen in FIG. 3C et seq. actually does not occur.

Engagement by rollers 70, 71 and initial deformation takes place starting with the position shown in FIG. 3C. Then, the tubular glass 3 is compressed by rollers 70, 71 which are moved radially inwards toward the center axis of the tubular glass. In the stage shown in FIG. 3E, forming mandrel 75 contacts the inner surface of the tubular glass and forms the channel of the syringe cone. In the stage shown in FIG. 3F, finally, the shaping of the syringe cone has already been completed. Subsequently, the molding tools are retracted from the molded syringe cone 35. Thus, all forming steps for forming the syringe cone 35 were performed with the same molding tools 70, 71, 75 and foot 76. Such a forming station therefore performs all hot forming steps on a portion of the glass precursor. Subsequently, the syringe flange or finger rest on the other end of the tubular glass can be formed.

Starting from the shaping stage as illustrated in FIG. 3E it can clearly be seen that radial compression on the syringe cone 35 results in a thickening of the wall thickness. Now there is an option to cause some material flow away from end 30 by setting an appropriate temperature distribution as described above. Also, a reduced wall thickness may be caused at the peripheral edges of the reshaped tubular glass in the transition area between syringe barrel 37 and syringe cone 35. This effect may be counteracted as well, by adjusting an axially inhomogeneous power input by controlling axial distribution of the laser power.

Figure 4:
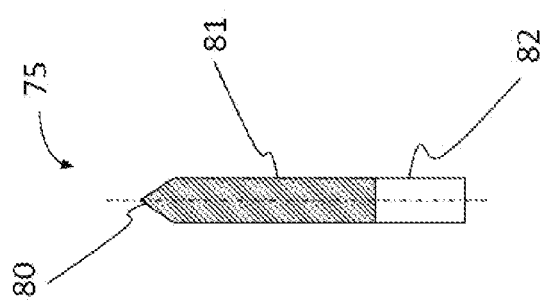
FIG. 4 is a plan view of a portion of a forming mandrel.

FIG. 4 illustrates a portion of a forming mandrel 75 in a plan view. Starting from the tip 80 of forming mandrel 75, a region of the forming mandrel 75 adjacent to the tip is marked, in which the forming mandrel 75 will or may contact the glass precursor during the reshaping process. A portion 82 is intended for retaining the forming mandrel 75.

According to the invention, forming mandrel 75 is made from an alloy which comprises at least a first temperature-stable core material. So the core material is the basic or base material of the forming mandrel 75 and is selected from the group of precious metals, in particular of platinum group elements. Accordingly, the forming mandrel is a solid forming mandrel, at least in the region 81 which serves for reshaping. Preferably, forming mandrel 75 is of monolithic configuration.

In the present example the core material is a precious metal, preferably platinum or iridium, or an appropriate platinum or iridium alloy. In addition to iridium and/or platinum, the core material of forming mandrel 75 may include palladium, rhodium, rhenium and/or ruthenium, or a corresponding alloy.

In addition to the core material, the forming mandrel 75 includes another alloying element which is selected from the group consisting of tungsten, zirconium, rhodium, molybdenum, and rhenium. The amount of these alloying elements is advantageously in a range of at least 0.1 wt %, preferably at least 0.3 wt %, more preferably 0.5 wt % and most preferably at least 0.9 wt %, and not more than 10 wt %, preferably at most 6 wt %, and more preferably at most 5 wt %.

In a first embodiment, the core material of the forming mandrel 75 comprises at least 20 wt % of platinum or an alloy including at least 20 wt % of platinum.

In another embodiment, the core material comprises at least 5 wt % of rhodium or an alloy including at least 5 wt % of rhodium.

In a further preferred embodiment, the core material comprises a platinum-rhodium alloy with at least 20 wt % of platinum and at least 5 wt % of rhodium.

In yet another embodiment, the core material comprises a platinum-nickel alloy including at least 5 wt % of nickel.

In yet another preferred embodiment, the core material comprises a platinum-iridium alloy including at least 5 wt %, preferably at least 10 wt %, and more preferably at least 20 wt % of iridium.

In yet another preferred embodiment, the core material comprises at least 20 wt %, preferably at least 50 wt %, more preferably at least 70 wt %, and most preferably at least 90 wt % of iridium as an alloying element.

In an especially preferred embodiment, iridium is chosen as the core material for the forming mandrel 75, and tungsten as the alloying element.

Very suitable for reshaping a tubular glass made of borosilicate glass using a molding tool 1 as described above is a material for the forming mandrel 75 which comprises an iridium-tungsten alloy with at least 0.01 wt %, 0.05 wt %, 0.1 wt %, preferably at least 0.3 wt %, more preferably at least 0.5 wt %, and most preferably at least 1 wt % of tungsten. It is furthermore advantageous if the tungsten content is not more than 10 wt %, preferably at most 6 wt %, and more preferably at most 5 wt %. A particularly suitable forming mandrel 75 comprises an iridium-tungsten alloy with 0.96 wt %, 1.92 wt %, or 3.84 wt % of tungsten.

The comparatively high hardness and high recrystallization temperature of iridium have a very positive effect on the service life of forming mandrel 75 during the reshaping of borosilicate glass. This even enables reshaping processes at temperatures above 800° C. or above 900° C. This is further promoted by the high acid resistance of tungsten.

Even after a great many of processing cycles or reshaping operations, such as between 8,000 and 10,000 cycles, the forming mandrel 75 did not show any tendency to cracking on the surface or any other signs of wear.

Due to the low wear, in particular due to the low material erosion of the forming mandrel 75 comprising an iridium-tungsten alloy, it was observed that the degree of contamination with tungsten was very low.

It could be observed that the use of a forming mandrel 75 on the basis of an iridium-tungsten alloy with a tungsten content of about 1 wt % results in a particularly long service life of the forming mandrel 75. At the same time this low material erosion has the advantage that contamination with tungsten is particularly low.

Glass syringes, preferably made of borosilicate glass, which were reshaped using the aforementioned molding tool had a very low tungsten content in the reshaped cavity.

Syringes reshaped using forming mandrel 75 can be obtained which have a tungsten content within the cavity of the syringe of less than 50 ng, preferably less than 30 ng, more preferably less than 10 ng per syringe.

In a particularly preferred embodiment, the tungsten content within the cavity of a syringe that has been reshaped using the forming mandrel 75 is between 1 and 10 ng per syringe, preferably between 1 and 5 ng per syringe, and more preferably between 1 and 3 ng.

Thus, the manufacture of such syringes could be implemented with significant cost savings.

Figure 5:
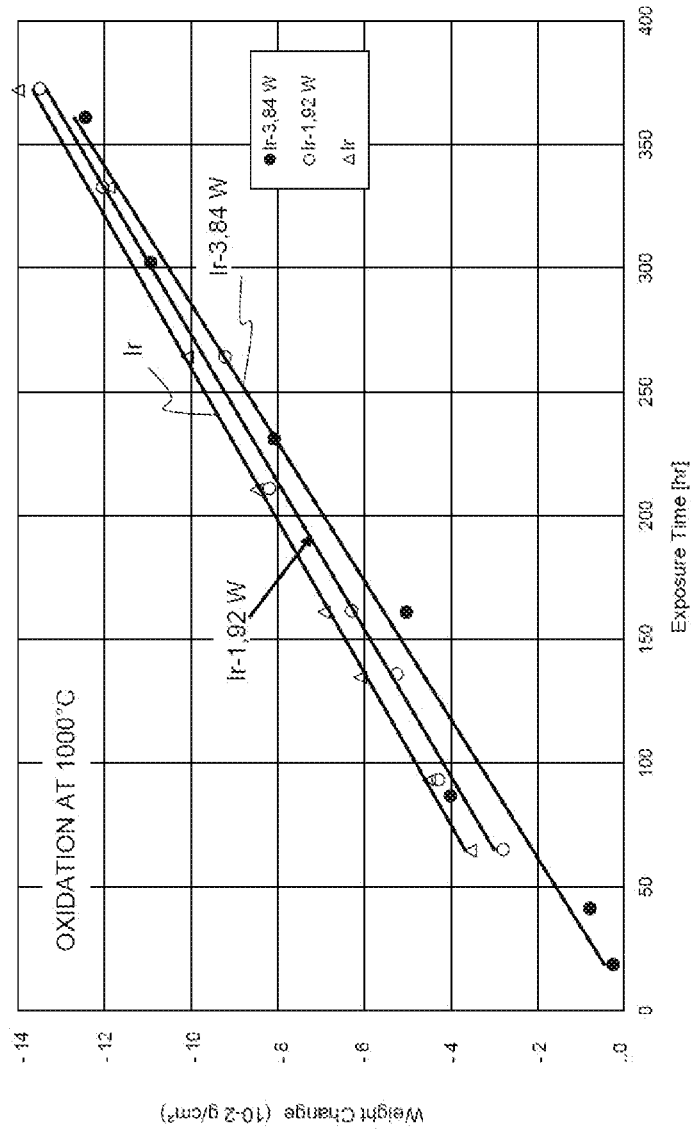
FIG. 5 is an overview of mass loss of different iridium-tungsten alloys at 1000° C.

FIG. 5 gives an overview of the mass loss of different iridium-tungsten alloys at 1000° C. (source: Liu, Inouye, December 1976 Oak Ridge National Laboratory, Tennessee). In the diagram the ordinate axis represents time in hours, and the abscissa axis represents weight change in $10^{-2}$ g/cm$^2$.

Samples made of three different alloys were exposed to a temperature of 1000° C., and material erosion was measured. Besides pure iridium, two iridium-tungsten alloys with 1.92 wt % of tungsten and 3.84 wt % of tungsten (Ir-1.94W, Ir-3.84W) were compared with each other in terms of material erosion. The diagram shows that material loss depends on the content of tungsten and decreases with higher tungsten contents.

The advantages of iridium-tungsten alloys are on the one hand the long service life, combined with a high dimensional tolerance. Mass loss due to a formation of volatile oxides is significantly reduced compared to pure iridium because of the tungsten content so that no measurable material erosion is detectable at the iridium mandrel. The low material erosion on the forming mandrel provides for a consistently high dimensional tolerance of the cone channel during manufacturing, with a very narrow tolerance.

Furthermore, the forming mandrel based on an iridium-tungsten alloy is characterized by low reactivity to glass constituents. For example, iridium as a precious metal only exhibits minor reactivity to glass evaporation products such as alkali oxides or boron oxides, so that corrosion is substantially suppressed.

Introduction of contamination into the reshaped glass product is very low and hardly measurable by chemical analysis.

Moreover, there is no deposition formed in the cone channel, e.g. of oxide particles.

Therefore, the molding tool of the invention, in particular the forming mandrel 75 according to the invention brings about several advantages which make the molding tool considered to be particularly suitable for the production of low-tungsten pharmaceutical packaging, such as in particular syringes.

What is claimed is:

1. A molding tool for reshaping hollow-body glass precursors, comprising a forming mandrel for reshaping at least a portion of a heated region of the glass precursor, the forming mandrel comprising a temperature-stable core material and an alloying element, the core material comprises a precious metal selected from the group consisting of iridium, palladium, rhenium, ruthenium, and any combinations or alloys based thereon, and the alloying element comprises tungsten in an amount of at least 0.01 wt % wherein the forming mandrel is configured to be introduced into an interior of each hollow-body glass precursor and configured to prevent introduction of impurities into an interior of the hollow-body glass precursors.

2. The molding tool as claimed in claim 1, wherein the alloying element further comprises a material selected from the group consisting of zirconium, rhodium, molybdenum, ruthenium, and rhenium.

3. The molding tool as claimed in claim 1, wherein the core material further comprises a material selected from the group consisting of platinum, rhodium, and any combinations or alloys based thereon.

4. The molding tool as claimed in claim 1, wherein the core material further comprises at least 20 wt % of platinum.

5. The molding tool as claimed in claim 1, wherein the core material further comprises at least 5 wt % of rhodium.

6. The molding tool as claimed in claim 1, wherein the core material is a platinum-rhodium alloy including at least 20 wt % of platinum and at least 5 wt % of rhodium.

7. The molding tool as claimed in claim 1, wherein the core material is a platinum-rhodium alloy including at least 25 wt % of platinum and at least 7 wt % of rhodium.

8. The molding tool as claimed in claim 1, wherein the core material is a platinum-rhodium alloy including at least 30 wt % of platinum and at least 10 wt % of rhodium.

9. The molding tool as claimed in claim 1, wherein the core material is a platinum-nickel alloy including at least 5 wt % of nickel.

10. The molding tool as claimed in claim 1, wherein the core material is a platinum-iridium alloy including at least 5 wt % of iridium.

11. The molding tool as claimed in claim 1, wherein the core material is a platinum-iridium alloy including at least 20 wt % of iridium.

12. The molding tool as claimed in claim 1, wherein the core material comprises at least 20 wt % of iridium.

13. The molding tool as claimed in claim 1, wherein the core material comprises at least 90 wt % of iridium.

14. The molding tool as claimed in claim 1, wherein the amount of the tungsten is at least 0.9 wt %.

15. The molding tool as claimed in claim 1, wherein the amount of the tungsten is at most 5 wt %.

16. The molding tool as claimed in claim 1, wherein the core material is an iridium-tungsten alloy with at least 0.1 wt % of tungsten.

17. The molding tool as claimed in claim 16, wherein the iridium-tungsten alloy comprises 0.96 wt % of tungsten, or 1.92 wt % of tungsten, or 3.84 wt % of tungsten.

18. An apparatus for reshaping hollow-body glass precursors, comprising:
a heater configured to locally heat a region of the glass precursor to above a softening point; and
a molding tool having a forming mandrel for reshaping at least a portion of the region of the glass precursor, the forming mandrel comprising a temperature-stable core material and an alloying element, the core material comprises a precious metal selected from the group consisting of iridium, palladium, rhenium, ruthenium, and any combinations or alloys based thereon, and the alloying element comprises tungsten in an amount of at least 0.01 wt %, wherein the forming mandrel is configured to be introduced into an interior of each hollow-body glass precursor and configured to prevent introduction of impurities into an interior of the hollow-body glass precursors.

19. The apparatus as claimed in claim 18, wherein the heater is a laser and the apparatus further comprises a rotation device configured to rotate the molding tool and the glass precursor relative to each other, wherein the molding tool is configured so that a surface area of the portion is not covered by the molding tool so that, during reshaping, light from the laser is irradiated onto the portion.

20. A molding tool for reshaping hollow-body glass precursors, comprising:
a forming mandrel comprising a temperature-stable core material and an alloying element,
wherein the core material comprises a precious metal selected from the group consisting of iridium, palladium, rhenium, ruthenium, and any combinations or alloys based thereon, and
wherein the alloying element comprises tungsten in an amount of at least 0.01 wt % and a material selected from the group consisting of zirconium, rhodium, molybdenum, ruthenium, and rhenium, wherein the forming mandrel is configured to be introduced into an interior of each hollow-body glass precursor and configured to prevent introduction of impurities into an interior of the hollow-body glass precursors.

21. A molding tool for reshaping hollow-body glass precursors, comprising:
a forming mandrel for reshaping at least a portion of a heated region of the glass precursor, the forming mandrel comprising a temperature-stable core material and an alloying element,
wherein the temperature-stable core material comprises a material selected from the platinum group elements,
wherein the alloying element comprises tungsten in an amount of at least 0.01 wt % and a material selected from the group consisting of zirconium, rhodium, molybdenum, ruthenium, and rhenium, wherein the forming mandrel is configured to be introduced into an interior of each hollow-body glass precursor and configured to prevent introduction of impurities into an interior of the hollow-body glass precursors.

22. The molding tool as claimed in claim 21, wherein the amount of the tungsten is at least 0.9 wt %.

23. The molding tool as claimed in claim 21, wherein the amount of the tungsten is at most 5 wt %.

* * * * *